United States Patent [19]

Morelle et al.

[11] Patent Number: 5,504,228

[45] Date of Patent: Apr. 2, 1996

[54] NEW ACYLAMINO ACIDS

[75] Inventors: Jean Morelle; Eliane Lauzanne, both of Paris; Jacqueline Rothfuss, Lauterbourg, all of France

[73] Assignee: Laboratoires Phytocos, France

[21] Appl. No.: 163,857

[22] Filed: Dec. 7, 1993

[30] Foreign Application Priority Data

Dec. 9, 1992 [FR] France .................................. 92 14840

[51] Int. Cl.$^6$ .................................................. C07C 237/12
[52] U.S. Cl. .................. 554/69; 554/68; 554/63; 562/516
[58] Field of Search .................. 554/63, 68, 69; 514/547; 564/192, 215; 8/128.1; 562/516

[56] References Cited

U.S. PATENT DOCUMENTS

| | | | |
|---|---|---|---|
| 4,089,954 | 5/1978 | Morelle et al. | 424/245 |
| 4,112,085 | 9/1978 | Morelle et al. | 424/245 |

FOREIGN PATENT DOCUMENTS 61-069714  4/1986  Japan .

OTHER PUBLICATIONS

Chemical Abstract, vol. 102, #14, p. 295, 59982d, 1984.
Abstract of JP-61-069714, 1986.
Tsukada et al, Journal of Applied Polymer Science vol. 45, #10, pp. 1719–1725, 1992.
G. S. Nadiger et al., "Investigation of amino acid composition in the crystaline region of silk fibroin" CHEM. ABST., vol. 102, No. 14, Apr. 8, 1975, p. 78.
Ichimaru Farukosu K. K., "Cosmetics containing oil–soluble silk peptides", CHEM. ABST., vol. 101, No. 8, Aug. 20, 1984, p. 295.

*Primary Examiner*—José G. Dees
*Assistant Examiner*—Deborah D. Carr
*Attorney, Agent, or Firm*—Lucas & Just

[57] ABSTRACT

The invention relates to new acylamino acids obtained by acylation of hydrolysates of proteins containing, essentially, fibroin and sericin as, for instance, silk.

The invention provides also various compositions containing the said acylamino acids, for use in the cosmetic, hygienic, therapeutic and agricultural fields.

10 Claims, No Drawings

NEW ACYLAMINO ACIDS

The present invention relates to new acylamino acids, which are compounds resulting from the acylation, by an organic or a fatty acid, of peptides or of amino acids, obtained by the hydrolysis of particular proteins.

The invention relates, more particularly, to acylamino acids obtained by acylating the total hydrolysates of proteins containing, essentially, fibroin and sericin.

In this field, the state of the art may be illustrated by the publications Chemical Abstract Volume 101, 1984, 59982d and Chemical Abstract Volume 102, 1985, 115009b, together with French patents No. 2 289 179, No. 2 411 006 and No. 2 422 400.

Acylamino acids and, more specifically, lipoamino acids obtained by the acylation, by a fatty chain, of amino acids or of short peptides, obtained by hydrolysis of animal proteins, are the subject of many patents disclosing their preparation, as well as their various uses, principally for cosmetics, pharmacy and agriculture.

In the field of cosmetics and pharmacy, the use of these compounds gives rise to a relative suspicion, in so far animal tissues from which they are issued, might induce a contamination by pathogen agents, such as bacteria and viruses.

Therefore, recently, in order to avoid such risks, vegetal proteins were foreseen, more particularly those issued from oilseeds, characterised by their high content in essential amino acids.

These acylamino acids, prepared from animal or vegetal proteins, often present the drawback of a more or less agreeable smell, which limits their use, especially in the field of cosmetics.

The purpose of the present invention is to propose new acylamino acids structures, which do not present drawback as to the smell, which are obtained by the acylation of the total hydrolysates of proteins essentially containing fibroin and sericin and, preferably, proteins secreted by Bombyx Mori, which corresponds to the silk and contains significant amounts of polypeptidic structures, fibroin and sericin. The total hydrolysis leads to the releasing of the amino acids which, together, represent about 90% of the total: glycine, whose average content is of from 45 to 50%

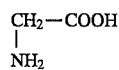

alanine, which represents 28 to 30% of the polypeptidic chains

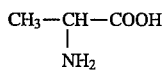

and serine, characterised by an hydroxy function, whose content is of from 10 to 15%

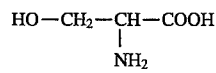

As to the other amino acids, their contents do not exceed 5% for tyrosine, 2% for valine and 1% for the other (cf. "The chemical structure and the crystalline structure of Bombyx Mori Silk fibroin"—LOTZ-COLONA CESARI—Biochimie 1979, (61), 205–214 and "HPLC fractionation of C5 peptides of Bombyx Mori Silk Fibroin"— FREDDI, FARAGO and MAIFRENI, Sericologia 29 (3), 307–326).

Taking into account the rather important volume of the fibres, the hydrolysis is executed in two steps. For the degradation of the fibres, in the first step, three parts of the fibres are placed in a solution containing three parts of hydrochloric acid at 33% and a part of water (parts in weight). The fibres disaggregate easily at a temperature of about 80° C., which reduces considerably the volume handled.

The second step consists of the total hydrolysis of the same, which requires about 4 hours, in order to obtain a solution which gives a negative biuret reaction. The hydrolysate is treated by a soda solution at 30%, for bringing the reaction mixture at about pH 5, then active charcoal is added for alecoloration, which will be easier, because there will be less cocoons and chrysalides, given that, for economical reasons, waste will be used, constituted of more or less agglomerated fibres, containing cocoons or chrysalides.

The titration of the hydrolysate is effected by formol titration, in order to determine the amount of acid chloride or of acid anhydride, of fatty or of organic acids, required for the acylation.

In the case of fatty chains from 5 carbon atoms (liposoluble products will be obtained), the acylation is effected by pouring the acylating agent in the hydrolysate, at temperatures between 15° and 50° C., according to the nature of the acylating agent, while maintaining the pH between 10 and 11. When the whole reagent is introduced, the temperature of the reaction medium is brought to 70° C. for one hour, in the case of fatty acids chloride. The temperature is cooled to less than 30° C., then hydrochloric acid is used to bring the medium to pH 1/1.5. A white voluminous matte is formed, containing about from 60 to 70% of water. This matte is then washed on the filter, to remove the hydrochloric acid, then dehydrated under reduced pressure, at a temperature below 50° C., in order to avoid coloration. According to the nature of the fatty chain, the liposoluble products obtained can be reduced to a powder or to a paste.

In the case of acyl chains containing of from 1 to 4 carbon atoms, acetyl, propionyl, butyryl (water-soluble products will be obtained), after the pH of the medium being brought to about 1/1.5, the hydrochloric acid issued from the reaction and the water are removed, by distillation under reduced pressure, the water-soluble acylamino acid being extracted by a solvent such as ethanol, for example.

The acylamino acids obtained according to the invention are mixtures of acylamino acids, corresponding to the following structures:

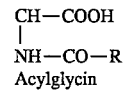
Acylglycin

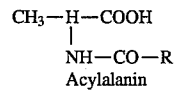
Acylalanin

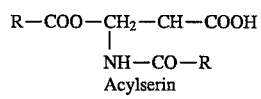
Acylserin wherein R represents a radical of fatty acid of from $C_5$ to $C_{30}$ or of an organic acid of from $C_1$ to $C_4$. Fibroinosericin acyls are then obtained, characterised by the above mentioned three amino acids and by minute amounts of the other classic amino acids, which are easily revealed by thin layer chromatography and which correspond exactly to the spots obtained on the hydrolysate of silk fibres, characterised by the three dominating spots of glycine, alanine and serine.

Examples of preparations of acylamino acids according to the invention

Example 1

Hydrolysis of silk waste comprising cocoons

In a reactor containing 300 ml of hydrochloric acid at 33% and 100 ml of water are progressively added, following the degradation of the fibres, 300 g of silk waste. The temperature is brought to about 100° C. and when the volume of the fibres is sufficiently reduced—which requires about one hour—to the boiling point, for about 4 hours. After cooling, the hydrolysate is brought to pH 5 by addition of a soda solution, then filtered in order to separate the water-carbonaceous elements of the cocoons. According to the content in cocoons, the hydrolysate is decolorated by addition of active charcoal, either at room temperature or at 80° C. The titration of the solution is determined by formol titration, the weight of the acylating agent is determined with regard to the $NH_2$ functions content of the amino acids released by the hydrolysis.

Example 2

Acylation by lauroyl chloride

To 200 ml of silk hydrolysate as obtained in example 1 and 400 ml of water, soda is added, under stirring, in order to bring the pH to 10.5. The lauroyl chloride is then poured dropwise, while maintaining the pH between 10.5 and 11, at a temperature between 30° and 40° C. When the whole content of chloride has been added, the temperature of the mixture is brought to 70° C., for about one hour. After cooling, a solution of hydrochloric acid is added, in order to bring the pH to about 1/1.5; the acylamino acid decants under the form of a whitish matte, which is thus washed with cool water, then dehydrated under reduced pressure, at a temperature lower than 50° C., in order to avoid colorations. There is obtained a product melting at 89°/90° C.

Example 3

Acylation by palmitoyl chloride

As for example 2, to 200 ml of silk hydrolysate obtained in example 1, under the same pH conditions, 96 g of palmitoyl chloride are added. After acylation and warming at 70° C. for about one hour, the mixture is cooled and the derivative is released by addition of hydrochloric acid. The matte is washed with cold water, then dried under reduced pressure. There is obtained a powder melting at 98°/99° C.

Example 4

Acylation by acetic anhydride 200 ml of silk hydrolysate as obtained in example 1 are brought to pH 10.5 and to a temperature not exceeding 20° C., the reaction mixture being maintained at this temperature by ice. Under stirring, 98 g of acetic anhydride are introduced, dropwise, while maintaining the pH between 10.5 and 11. When the whole anhydride has been used, the stirring is maintained during 30 minutes, then the mixture is acidified by HCl at 33%, so that a pH of from 1 to 1.5 is obtained. The water and the hydrochloric acid which is in excess are removed under reduced pressure. Finally, a mixture of sodium chloride and acetyl-fibroin-sericin is obtained which, recaptured by a solvent such as alcohol, allows to remove the sodium chloride by filtration. The acylamino acid crystallises in alcohol, under the form of small crystals, forming a waxy mass whose melting point is about 59°/60° C.

The hereinafter table gives the various analytic characteristics of the acylamino acids produced according to the invention:

| Acyls | Acetyl | Octanoyl | Undecylenoyl | Lauroyl | Palmitoyl | Oleoyl | Linoleoyl |
|---|---|---|---|---|---|---|---|
| Nitrogen | 7.5/8 | 5.8/6.5 | 4/4.5 | 3.8/4.4 | 3.5/4 | 2.5/2.8 | 1.8/2 |
| Acid index | 370 | 274/285 | 230/240 | 220/240 | 275/290 | 140/160 | 115/130 |

The invention relates also to various compositions prepared with the acylamino acids of the invention, said compositions being useful in the cosmetic, hygienic, therapeutic and agricultural fields.

The new acylamino acids may be used as such, i.e. under their acidic form, or under the form of their respective salts with alkali metals or organic bases, such as various amines or amino alcohols, or biological bases such as lysine, choline or ammonia; alkaline-earth metals are also usable and also the metals generally known as oligo-elements, such as iron, manganese, cobalt and copper.

The choice of the agent used for the salt formation will, of course, depend on the intended application of the compound.

For instance, for the production of detergent compositions, the preferred form is the salt with a mineral, organic or biological base, of the acylamino acid, whose acylating fraction corresponds to the lauric chain, as indicated in example 2. Thus, a product is obtained, principally intended for the bodily hygiene which, when used at 20%, gives foaming ability never reached with the other amino acids issued from animal or vegetable hydrolysates, by a very specific and exceptional sweetness and by a powerful washing action, these properties being due to the low molecular weights of the amino acids, especially the glycine. As mineral bases, soda or potash can be used, as organic bases, monoethanolamine and, as biological bases, lysine, choline or ammonia.

For anti-sudoral compositions, which will be able to inhibit hyperhidrose, there are used mono and dibasic aluminium salts, with acyl chains in $C_8$ and $C_{11}$.

Acylamino acids produced according to the invention allow to obtain substances which are particularly interesting in the cosmetic field, because they include serine, which is one of the principal constituents of silk which, under the acidic form, present the advantage of increasing water distribution in dehydrated or non-polar areas (A. KAPLAN: "Hydrogen bonding properties of N-Palmitoyl-Sérine"—Journal of colloid and interface Science, 1967 (25), 63–70) and being anti-toxic (MAC FARLANE: Adv Lipid Res., 1964 (2), 96–125).

On the basis of the present invention, anti-microbial, anti-fungic and anti-viral compositions will be produced (acylating agent in $C_8$ or $C_{11}$, acidic form), in this latest case, for example, active on herpes.

In the hygienic field, such as the protection against lice (antipediculosic *capitis et corporis*), acyl chains comprising of from 3 to 11 carbon atoms will be used, with acidic acylaminoacids.

In the agricultural field, described amino acyls in $C_8$ and $C_{22}$ will be preferably used, as their salts by oligo-elements, especially copper, as protecting agents of vegetables, or as stimulative agents for the development.

In the pharmaceutical field, anti-inflammatory compositions will be produced (acylating agent $C_8$ to $C_{22}$, acidic form), as treatment for eczema and intertrigo, for example, for the treatment of all the microbial, fungic or viral inflammations of the skin.

The hereinafter compositions are non-limitative examples of various compositions obtained according to the invention.

| 1 - Cosmetic composition (cream): | |
|---|---|
| Stearic acid | 8 |
| Cetyl alcohol | 2 |
| Polyoxyethyleneglycol stearate | 5 |
| Palmitoyl fibroin sericin | 4 |
| Glycerine | 10 |
| Water | qs 100 |
| 2 - Washing composition for the bodily hygiene: | |
| Lauroyl fibroin sodic sericin with 20% of dry extract | 30 |
| Octanoyl fibroin sericin | 0.5 |
| NaCl for increasing of the viscosity | 5 |
| Demineralized water | qs 100 |
| 3 - Toilet soap: | |
| Coprah soap | 95 |
| Lauroyl fibroin sericin | 5 |
| 4 - Anti-sudoral composition: | |
| Undecylenoyl-fibroin sericin salified by aluminium under a dibasic form | 5 |
| Glycerol palmitostearate | 5 |
| Polyoxyethylened cetyl alcohol | 8 |
| Propyleneglycol | 10 |
| Water | qs 100 |
| 5 - Anti-pediculosis composition: | |
| Octanoyl-fibroin-sericin | 3 |
| Alcohol at 30° | 97 |
| 6 - Anti-acne anti-septic composition: | |
| Octanoyl-fibroin-sericin | 4 |
| Fatty polyoxyethylened alcohol | 5 |
| Water | 91 |
| 7 - Composition for the protection of vegetables: | |
| Octanoyl-fibroin-sericin salified by copper | 5 |
| Ammonia solution at 30% | 5 |
| Water | qs100 |

We claim:

1. Acylamino acids resulting from the acylation, by an acyl radical consisting of from 1 to 30 carbon atoms, of a mixture of amino acids obtained by total hydrolysis of a protein characterized by the fact that the protein comprises significant quantities of fibroin and sericin and that the total hydrolysis of the protein results in individual amino acids.

2. Acylamino acids according to claim 1, characterized by the fact that the protein is Bombyx Mori.

3. Acylamino acids according to claim 1, wherein the protein is issued from silk waste, under the form of fibres comprising cocoons or chrysalides.

4. Acylamino acids according to claim 2, wherein the protein is issued from silk waste, under the form of fibres comprising cocoons or chrysalides.

5. Acylamino acids according to claim 1, characterized by the fact that the mixture of amino acids which have to be acylated essentially contains glycine, alanine and serine, these three amino acids representing 90% of the total of amino acids, in proportions comprised between 45 and 60% for glycine, between 20 and 30% for alanine and between 10 and 15% for serine.

6. Acylamino acids according to claim 2, characterized by the fact that the mixture of amino acids which have to be acylated essentially contains glycine, alanine and serine, these three amino acids representing 90% of the total of amino acids, in proportions comprised between 45 and 60% for glycine, between 20 and 30% for alanine and between 10 and 15% for serine.

7. Acylamino acids according to claim 3, characterized by the fact that the mixture of amino acids which have to be acylated essentially contains glycine, alanine and serine, these three amino acids representing 90% of the total of amino acids, in proportions comprised between 45 and 60% for glycine, between 20 and 30% for alanine and between 10 and 15% for serine.

8. Acylamino acids according to any one of claims 1 to 3 or 4 to 7, characterized by the fact that they are salified by the mineral bases soda or potash, or by organic bases ammonia, ethanol amines or by biological bases lysine or choline.

9. Acylamino acids according to claim 8, characterized by the fact that the acylating agent is the lauric chain in $C_{12}$.

10. Acylamino acids according to any one of claims 1 to 3 or 4 to 7, characterized by the fact that they are salified by oligo-elements, by alkaline-earth metals or by aluminum.

* * * * *

UNITED STATES PATENT AND TRADEMARK OFFICE
CERTIFICATE OF CORRECTION

PATENT NO. : 5,504,228
DATED : April 2, 1996
INVENTOR(S) : Jean Morelle et al.

It is certified that error appears in the above-indentified patent and that said Letters Patent is hereby corrected as shown below:

Column 1, line 33, change "drawback" to --drawbacks--.

Column 2, line 4, change "disagregate" to --disaggregate--; line 13, change "alecoloration" to --decoloration--.

Column 4, line 9, change "to remove" to --for removal of--; line 57, change "to obtain" to --for obtention of--.

Column 5, line 37, change "salilied" to --salified--; line 51, change "salilied" to --salified--.

Column 6, line 24 (claim 5), change "comprised" to --comprising--.

Column 6, line 32 (claim 6), change "comprised" to --comprising--.

Column 6, line 39 (claim 7), change "comprised" to --comprising--.

Signed and Sealed this

Twentieth Day of August, 1996

Attest:

BRUCE LEHMAN

*Attesting Officer*  *Commissioner of Patents and Trademarks*